United States Patent [19]

Spencer et al.

[11] Patent Number: 5,759,502

[45] Date of Patent: Jun. 2, 1998

[54] INSTRUMENT CASSETTE HAVING A MECHANISM TO PREVENT LATERAL MOVEMENT OF AN INSTRUMENT SUPPORT RELATIVE TO AN INSTRUMENT SUPPORT HOLDER

[75] Inventors: Stephen F. Spencer, Greenwood; Cary A. Bettenhausen; Todd E. Bettenhausen, both of Indianapolis, all of Ind.

[73] Assignee: Sterilization Cassette Systems, Inc., Greenwood, Ind.

[21] Appl. No.: 792,507

[22] Filed: Jan. 31, 1997

[51] Int. Cl.⁶ ........................................... A61L 2/16
[52] U.S. Cl. .................... 422/300; 422/297; 206/370; 206/63.5; 211/60.1
[58] Field of Search .................... 422/297, 300; 206/369, 370, 438, 63.5; 211/60.1, 86

[56] References Cited

U.S. PATENT DOCUMENTS

| | | |
|---|---|---|
| 4,135,868 | 1/1979 | Schainholz . |
| 4,762,688 | 8/1988 | Berry, Jr. . |
| 4,854,475 | 8/1989 | Riihimaki et al. . |
| 5,173,273 | 12/1992 | Brewer . |
| 5,384,103 | 1/1995 | Miller . |
| 5,441,709 | 8/1995 | Berry, Jr. . |
| 5,492,671 | 2/1996 | Krafft . |
| 5,540,901 | 7/1996 | Riley . |

OTHER PUBLICATIONS

Advertisement for American Container Technology, Inc., p. 21 of *Surgical Products*, Sep. 1992 vol. 12, No. 1.
Advertisement for Micromedics, Inc., p. 1 of *Surgical Products*, Sep. 1993, vol. 12, No. 9.
Advertisement for American Container Technology, Inc., p. 11 of *Surgical Products*, Jul. 1992, vol. 11, No. 9.
Advertisement for Micromedics, Inc., p. 30 of *Surgical Products*, Jul. 1992, vol. 11, No. 9.
Advertisement for Micromedics, Inc., p. 23 of *Hospital Purchasing News*, Aug. 15, 1992, vol. 16, No. 8.

*Primary Examiner*—Robert J. Warden
*Assistant Examiner*—E. Leigh McKane
*Attorney, Agent, or Firm*—Maginot, Addison & Moore

[57] ABSTRACT

An instrument cassette includes a wall having a first hole defined therein. The instrument cassette further includes a holder having a channel and a second hole defined therein. The instrument cassette also includes an instrument support positioned within the channel of the holder. The instrument support has a blocking notch defined therein. The instrument cassette includes a screw which extends through the first hole and the second hole. The instrument cassette further includes a nut positioned within the blocking notch and secured to the screw.

5 Claims, 11 Drawing Sheets

INSTRUMENT CASSETTE HAVING A MECHANISM TO PREVENT LATERAL MOVEMENT OF AN INSTRUMENT SUPPORT RELATIVE TO AN INSTRUMENT SUPPORT HOLDER

CROSS REFERENCE

Cross reference is made to copending U.S. patent application Ser. No. 08/792,503 (Attorney Docket No. 3046), entitled "Instrument Cassette Having an Instrument Support Holder with Elongated Slots for Positioning the Instrument Support Holder in Numerous Orientations" by Cary Bettenhausen and Todd Bettenhausen, which is assigned to the same assignee as the present invention, and which is filed concurrently herewith.

BACKGROUND OF THE INVENTION

The present invention relates generally to a cassette used to hold medical or dental instruments, and more particularly, to an instrument cassette having a mechanism to prevent lateral movement of an instrument support relative to an instrument support holder.

Medical or dental instruments must be sterilized before they are used. Typically, after each use, the instruments are secured in a container known as an instrument cassette. Thereafter, the instrument cassette, along with the medical or dental instruments therein, is placed into a cleaning system wherein residual substances from a previous medical or dental procedure are removed from the instruments.

Instrument cassettes which have heretofore been designed typically include a number of instrument supports. The instrument supports typically have a number of slots or sockets defined therein which are configured so as to receive and hold the medical or dental instruments in place during the cleaning, sterilization, and storage thereof.

One drawback to many instrument cassettes which have heretofore been designed is that the instrument supports accommodate only a limited number of shapes or types of instruments. More specifically, many instrument cassettes include instrument supports which accommodate only a limited number of shapes or types of medical or dental instruments such as those medical or dental instruments associated with a single manufacturer. Hence, a user of the instrument cassette may be required to purchase a different, dedicated instrument cassette for each different shape or type (i.e. different instrument manufacturer) of medical or dental instrument.

The use of different, dedicated instrument cassettes for each shape or type of medical or dental instrument is undesirable in that inventory costs associated with the instrument cassettes are increased. More specifically, if a different, dedicated instrument cassette is required for each type of medical or dental instrument, the user of the instrument cassette is required to purchase and maintain a larger number of instrument cassettes as compared to if a single instrument cassette could be used for more than one type of medical or dental instrument.

To overcome this drawback, instrument cassettes have heretofore been designed with instrument supports which are interchangeable. More specifically, a number of instrument cassette designs include instrument supports which may be removed from the instrument cassette and exchanged for a different instrument support thereby enhancing the flexibility of the instrument cassette. Such interchangeable instrument supports are desirable in that the instrument support may be quickly and easily changed in order to change the type or shape of the medical or dental instrument which may be accommodated by the instrument cassette. In addition, it is desirable to quickly and easily change an existing instrument support for an identical replacement instrument support in the event that the existing instrument support wears out or is accidentally damaged.

However, interchangeable instrument supports often do not have the stability of instrument supports which are permanently affixed to the instrument cassette. In particular, interchangeable instrument supports which have heretofore been designed may slide or otherwise move within an instrument support holder associated with the instrument support thereby reducing the stability of the instrument support.

What is needed therefore is an instrument cassette that is configured so as to permit the cleaning, sterilization, and storage of multiple types (i.e. sizes and shapes) of medical or dental instruments. What is further needed is an instrument cassette which includes instrument supports which may be quickly and easily changed. What is also needed is an instrument cassette which has an instrument support which does not move relative to the instrument support holder.

SUMMARY OF THE INVENTION

According to a first embodiment of the present invention, there is provided an instrument cassette. The instrument cassette includes a wall having a first hole defined therein. The instrument cassette further includes a holder having a channel and a second hole defined therein. The instrument cassette also includes an instrument support positioned within the channel of the holder. The instrument support has a blocking notch defined therein. The instrument cassette includes a screw which extends through the first hole and the second hole. The instrument cassette further includes a nut positioned within the blocking notch and secured to the screw.

According to a second embodiment of the present invention there is provided an instrument cassette. The instrument cassette includes a wall. The instrument cassette also includes a holder secured to the wall. Moreover, the instrument cassette includes an instrument support secured to the holder. The instrument support has a blocking notch defined therein. The instrument cassette includes a blocking member positioned within the blocking notch and secured to the holder.

According to a third embodiment of the present invention, there is provided an instrument cassette. The instrument cassette includes a tray. The instrument cassette also includes a lid pivotally attached to the tray. Moreover, the instrument cassette includes a holder secured to the tray. The instrument cassette further includes an instrument support secured to the holder. The instrument support has a blocking notch defined therein. The instrument cassette further includes a mechanism, which cooperates with the blocking notch, for preventing lateral movement of the instrument support relative to the holder.

It is therefore an object of the present invention to provide a new and useful instrument cassette.

It is another object of the present invention to provide an improved instrument cassette.

It is a further object of the present invention to provide an instrument cassette that is configured so as to permit the cleaning, sterilization, and storage of multiple types (i.e. sizes and shapes) of medical or dental instruments.

It is yet another object of the present invention to provide an instrument cassette which includes instrument supports which may be quickly and easily changed.

It is moreover an object of the present invention to provide an instrument cassette which has an instrument support which does not move relative to the instrument support holder.

It is an additional object of the present invention to provide an instrument cassette which has instrument supports which are stable yet may be quickly and easily changed.

The above and other objects, features, and advantages of the present invention will become apparent from the following description and the attached drawings.

DETAILED DESCRIPTION OF THE INVENTION

Figure 1:
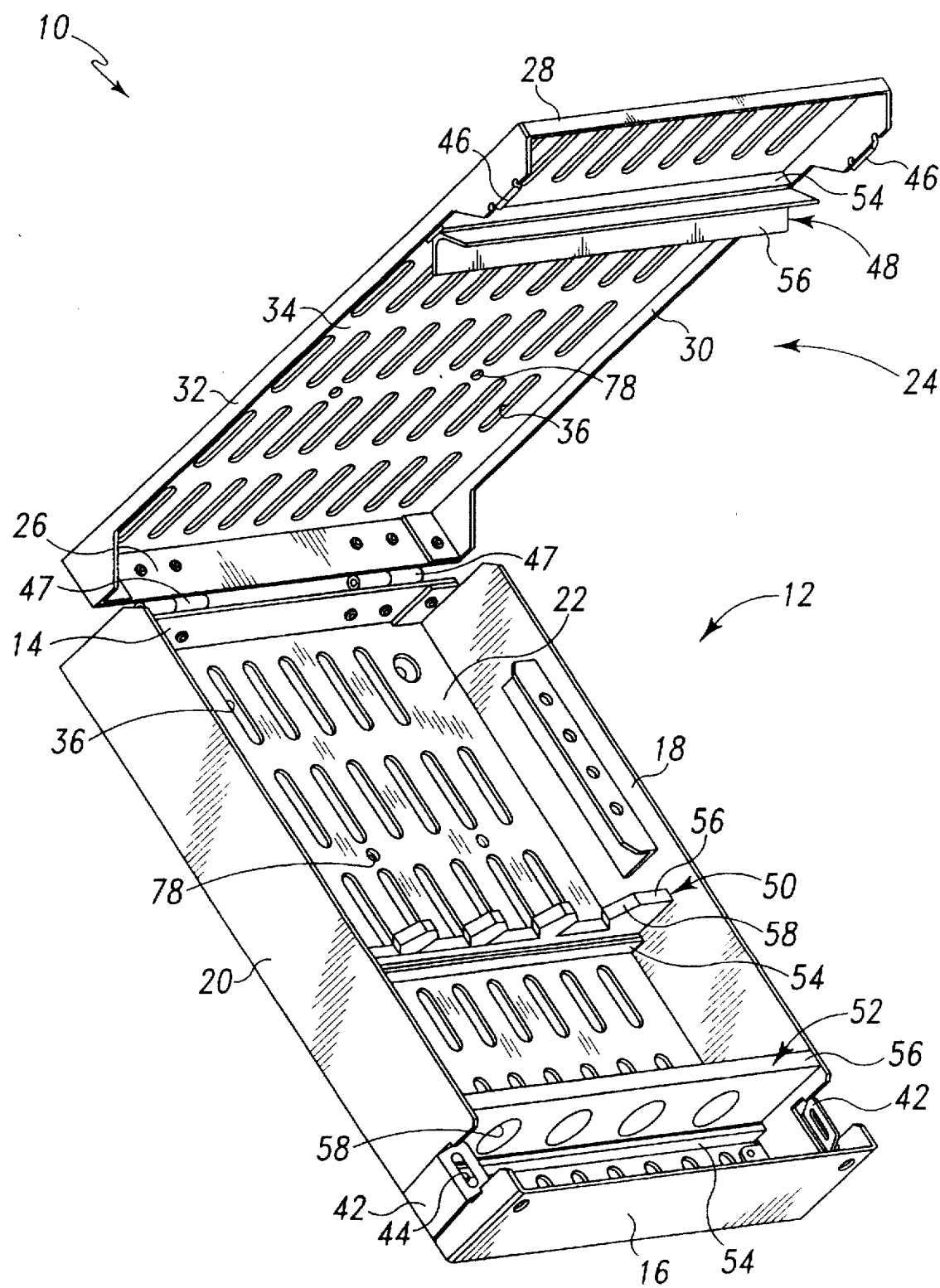
FIG. 1 is a perspective view of an instrument cassette which incorporates the features of the present invention therein, with the instrument cassette shown in an open position and oriented so as to enable viewing of an interior surface thereof.

While the invention is susceptible to various modifications and alternative forms, a number of specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 2:
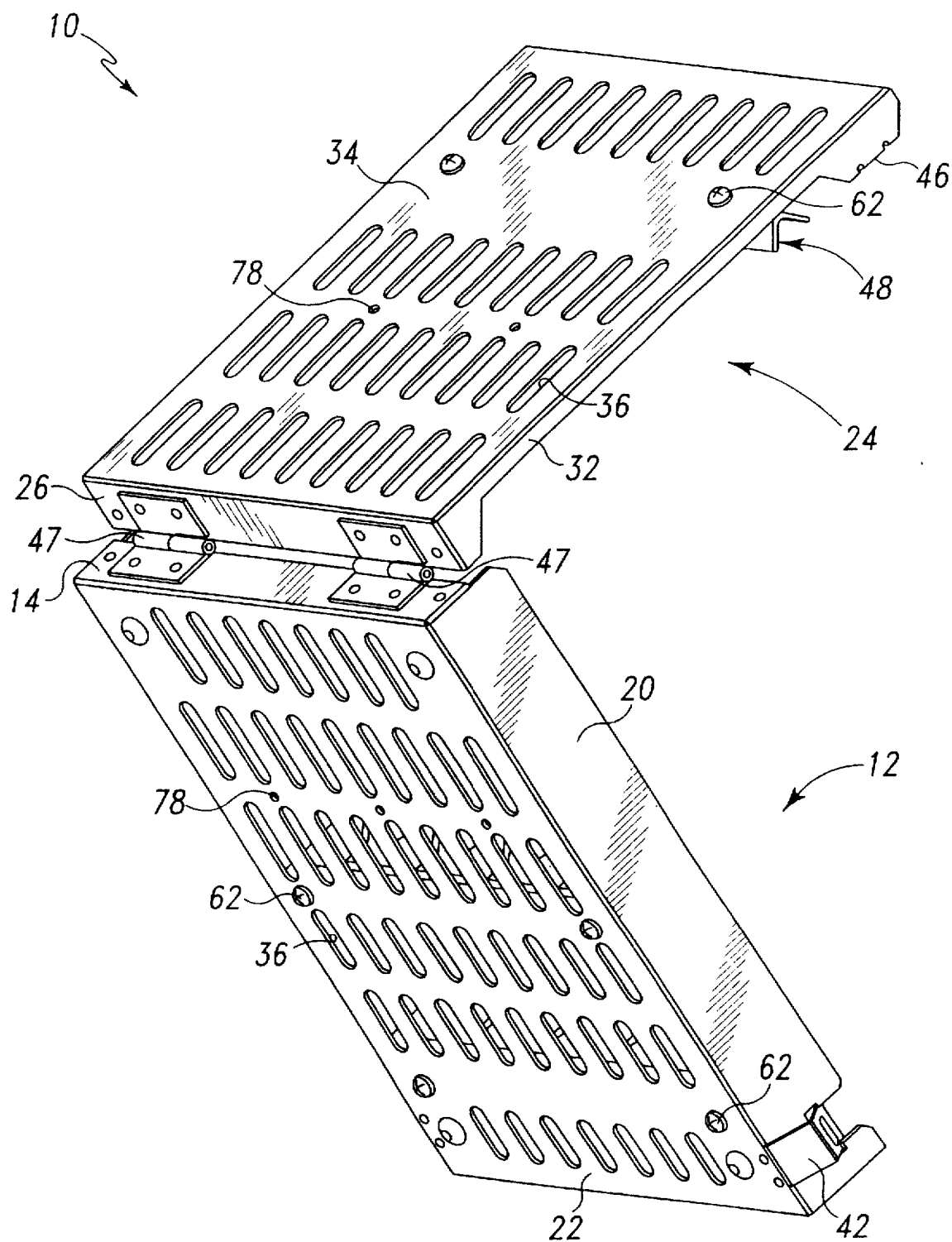
FIG. 2 is a view similar to FIG. 1 except that the instrument cassette has been rotated so as to enable viewing of an exterior surface thereof.
Figure 3:
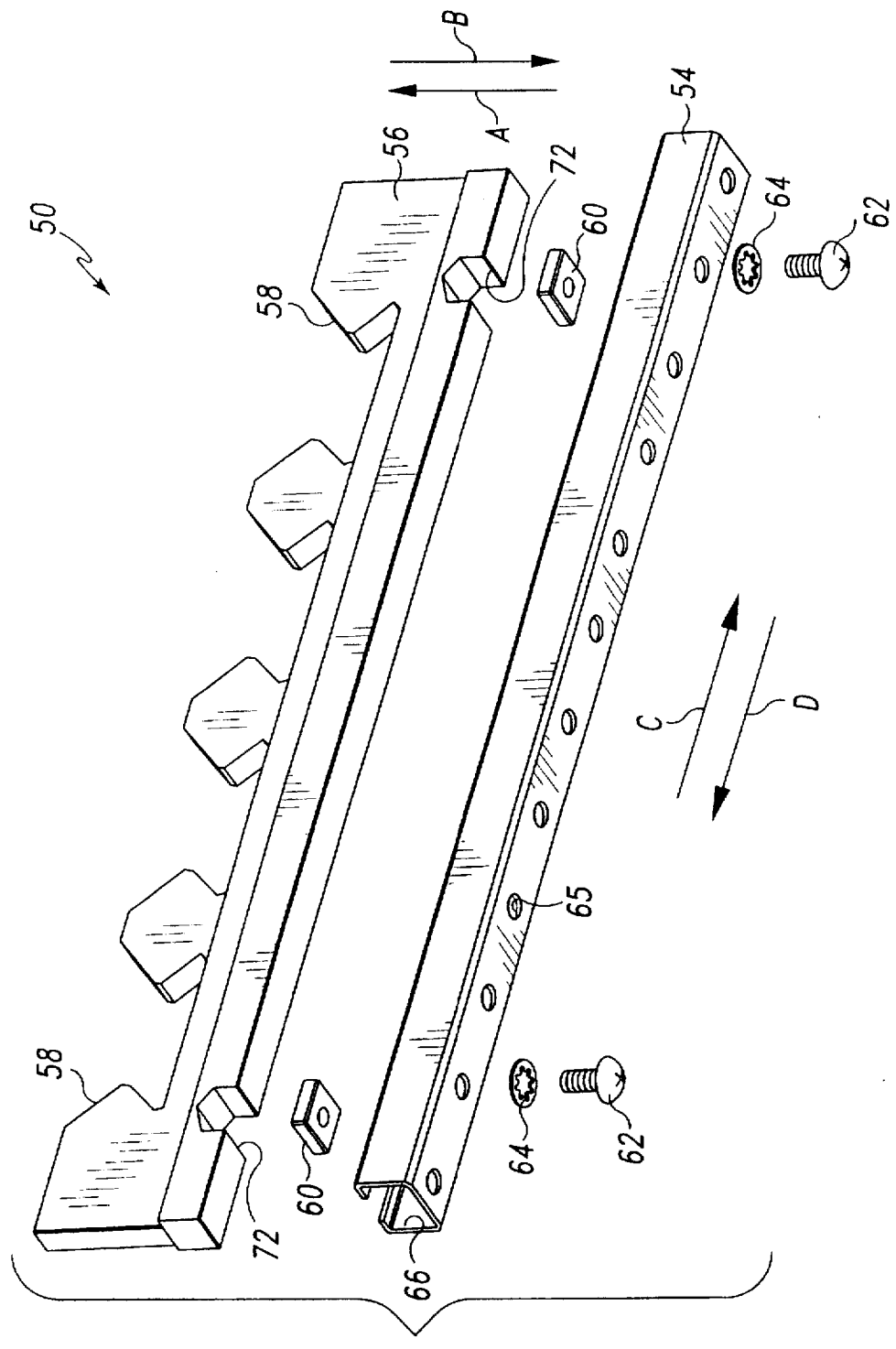
FIG. 3 is an enlarged exploded perspective view of one of the instrument retainer assemblies of the instrument cassette of FIG. 1.

Referring now to FIGS. 1 and 2, there is shown an instrument cassette 10. The instrument cassette 10 is used to hold medical or dental instruments and permits cleaning, sterilization, and storage of such instruments while housed in the instrument cassette 10.

The instrument cassette 10 includes a tray 12 and a lid 24. The tray 12 includes a bottom wall 22. A plurality of side walls 14, 16, 18, and 20 are attached in substantially perpendicular fashion to the periphery of the bottom wall 22. In particular, the side wall 14 is attached to a back edge of the bottom wall 22, whereas the sidewall 16 is attached to a front edge of the bottom wall 22 as shown in FIG. 1. In addition, the side wall 18 is attached to a right edge of the bottom wall 22, whereas the side wall 20 is attached to a left edge of the bottom wall 22. Collectively, the side walls 14, 16, 18, and 20 cooperate with the bottom wall 22 so as to provide a tray-like structure as shown in FIG. 1.

Similarly, the lid 24 includes a top wall 34. A plurality of side walls 26, 28, 30, and 32 are attached in substantially perpendicular fashion to the periphery of the top wall 34. In particular, the side wall 26 is attached to a back edge of the top wall 34, whereas the sidewall 28 is attached to a front edge of the top wall 34 as shown in FIG. 1. In addition, the side wall 30 is attached to a right edge of the top wall 34, whereas the side wall 32 is attached to a left edge of the top wall 34. Collectively, the side walls 26, 28, 30, and 32 cooperate with the top wall 34 to provide a tray-like structure as shown in FIG. 1.

A plurality of fluid holes 36 are defined in each of the bottom wall 22 and the top wall 34. The fluid holes 36 are provided so as to permit the ingress and egress of a sterilant such as steam.

A pair of hinge assemblies 47 couple the side wall 14 of the tray 12 to the side wall 26 of the lid 24. The hinge assemblies 47 cooperate so as to allow the lid 24 to pivot relative to the tray 12. The hinge assemblies 47 are shown riveted to the side walls 14 and 26, but it should be appreciated that the hinge assemblies 47 could be mechanically coupled to the side walls 14 and 26 with another type of fasteners such as screws.

The instrument cassette 10 includes a pair of latch members 42. A slot 44 is defined in each of the latch members 42. The slot 44 in each of the latch members 42 cooperates with a pair of tongues 46 defined in the lid 24. When each of the tongues 46 is received into the respective slot 44, the lid 24 is latched to the tray 12, thereby securing the medical or dental instruments within the cassette 10.

A number of the components of the instrument cassette 10 are made from stainless steel, or similar material. For example, the latch member 42 may be made from half-hard grade stainless steel 302. Also, the tray 12 and lid 24 may be made from stainless steel 304.

The instrument cassette 10 further includes a number of instrument retainer assemblies 48, 50, and 52. The instrument retainer assemblies 48, 50, and 52 hold or otherwise retain medical or dental instruments (not shown) during the cleaning and sterilization process, and the subsequent storage period until the instruments are next used.

Each of the instrument retainer assemblies 48, 50, and 52 includes a holder 54 and an instrument support 56. The instrument support 56 has a number of sockets 58 defined therein. The sockets 58 are configured so as to accommodate medical or dental instruments. The configuration of the sockets 58 may be altered or even eliminated, as shown in FIG. 1, to fit the needs of a given instrument support 56 so as to accommodate a given type of medical or dental instrument. It should be noted that the instrument retainer assemblies 48, 50, and 52 are substantially identical, except for the configuration of the various instrument supports 56 which are retained by a respective holder 54. Therefore, only a detailed discussion of one of the instrument retainer assemblies (i.e. instrument retainer 50) will be necessary.

The instrument retainer assembly 50 is shown in more detail in FIGS. 3–7. In addition to the holder 54 and the instrument support 56, the instrument retainer assembly 50 includes a pair of blocking members such as nuts 60, a pair of retaining members such as screws 62, and a pair of lock washers 64.

The holder 54 has a number of holes 65 defined therein. Moreover, the holder 54 has a channel 66 defined therein. A pair of retaining flanges 68 and 70 (see FIG. 6) are also included in the holder 54. As shall be discussed below, the retaining flanges 68 and 70 cooperate so as to retain the instrument support 56 within the holder 54.

As with the tray 12 and the lid 24, the holder 54 is made from stainless steel, or similar material. For example, the holder 54 may be made from stainless steel 304.

The instrument support 56 has a number of blocking notches 72 defined therein. Each of the blocking notches 72 is configured so as to receive one of the nuts 60. The nut 60 may be friction fit within the blocking notch 72.

The instrument support 56 is made from an elastomeric, silicone-based material. One type of silicone material which may be used is J7190-1-Blue.

Figure 4:
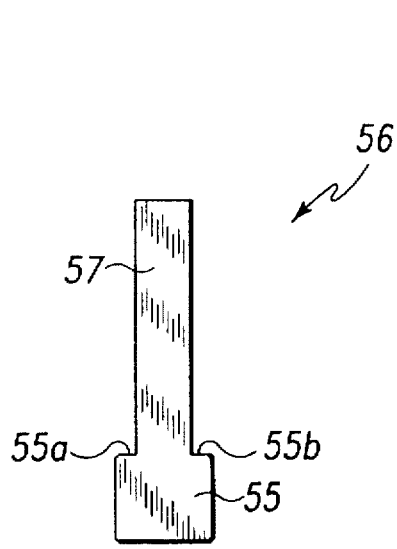
FIG. 4 is an enlarged elevational view of the instrument support of the instrument cassette of FIG. 1.
Figure 5:
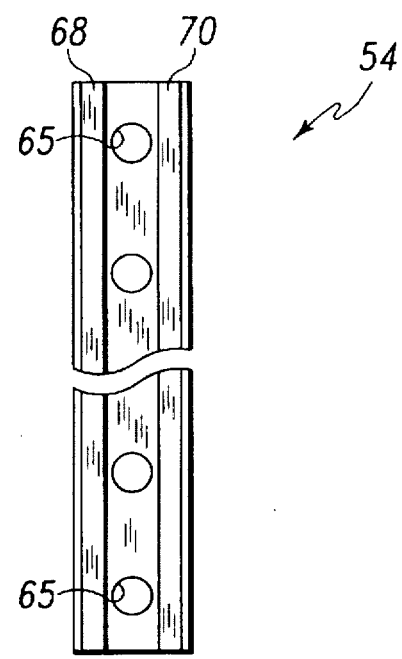
FIG. 5 is an enlarged fragmentary top elevational view of the holder of the instrument cassette of FIG. 1.

The instrument support 56 further includes a base portion 55 and an extending portion 57 which are integrally formed together. As shown in FIG. 4, the base portion 55 has a larger width than the extending portion 57. Moreover, the base portion 55 includes a pair of retaining surfaces 55a and 55b. In order to place the instrument support 56 in the holder 54, the base portion 55 is received into the channel 66 of the holder 54 in a friction fit manner (see FIG. 6). The retaining flanges 68 and 70 prevent vertical movement of the instrument support 56 within the channel 66. More specifically, the retaining flanges 68 and 70 cooperate with the retaining surfaces 55a and 55b, respectively, so as prevent the instrument support 56 from moving relative the holder 54 in the general directions of arrows A and B of FIG. 3.

The instrument retainer assembly 50 is secured to the bottom wall 22 of the tray 12 (see FIG. 1). In particular, one of the lock washers 64 is inserted onto the screw 62, and thereafter the screw 62 is received through one of a number of positioning holes 78 defined in the bottom wall 22 (see FIG. 1). The screw 62 is then received through one of the holes 65 defined in a first end of the holder 54 (see FIG. 3). After which, the screw 62 is threadingly engaged with a respective nut 60 disposed in the blocking notch 72. Another screw 62 is then engaged in the same manner with a second nut 60 at the other end of the holder 54 thereby securing the instrument retainer assembly 50 to the bottom wall 22 as shown in FIGS. 1 and 2.

Figure 6:
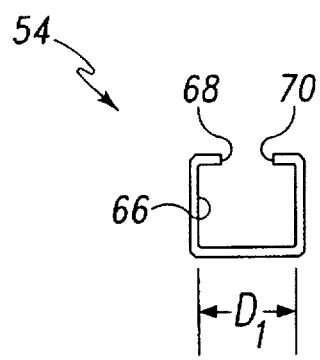
FIG. 6 is a side elevational view of the holder of FIG. 5.
Figure 7:
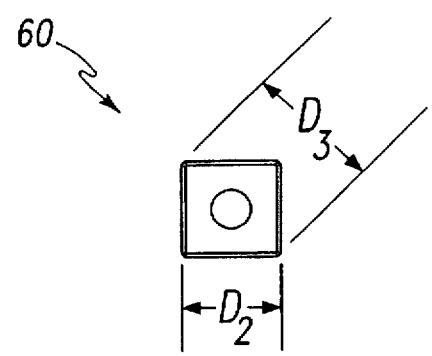
FIG. 7 is a top elevational view of the nut of the instrument retainer assembly of FIG. 3.

In addition to being friction fit within the blocking notch 72, the sizes of the channel 66 of the holder 54 and the nut 60 are configured to prevent rotation of the nut 60. In particular, the channel 66 has a width of a distance $D_1$ as shown in FIG. 6. In addition, an edge-to-edge width of the nut 60 is represented by a distance $D_2$ as shown in FIG. 7, whereas a corner-to-corner width is represented by a distance $D_3$. It should be appreciated that the distance $D_2$ is smaller in magnitude than the distance $D_1$ so as to allow the nut 60 to be received within the channel 66, but the distance $D_3$ is larger than the distance $D_1$ so as to prevent the nut 60 from rotating within the channel 66.

Once secured to the screw 62, the nut 60 prevents lateral movement of the instrument support 56 within the channel 66. More specifically, the nut 60 is prevented from moving within the channel 66 by the screw 62. In turn, the instrument support 56 is prevented from moving relative the holder 54 in the general directions of arrows C and D of FIG. 3 since the nut 60 is positioned within the blocking notch 72.

If it is desirable to remove the instrument retainer assembly 50 in order to change the location thereof on the bottom wall 22, the screws 62 must first be disengaged from the nuts 60. After which, the screws 62 are removed from the holes 65 in the holder 54. The screws 62 are then removed from the positioning holes 78 of the bottom wall 22. The holder 54, the instrument support 56, and the nuts 60 may then be collectively lifted away from the bottom wall 22, and repositioned proximate a different pair of positioning holes 78 (see FIG. 1). Thereafter, the screws 62 are re-engaged with the nuts 60 in the manner previously described above thereby re-securing the instrument retainer assembly 50 to the bottom wall 22.

If it is desirable to remove the instrument retainer assembly 50 in order to change the instrument support 56 (e.g. from one configuration of the sockets 58 to another), the screws 62 are disengaged from the nuts 60. After which, the screws 62 are removed from the holes 65 in the holder 54. The screws 62 are then removed from the positioning holes 78 of the bottom wall 22. The holder 54, the instrument support 56, and the nuts 60 may then be collectively lifted away from the bottom wall 22. The current instrument support 56, along with the nuts 60 which remain friction fit within the blocking notches 72, are then slid out of the channel 66 of the holder 54. After which, the nuts 60 are removed from the blocking notches 72. Thereafter, the nuts 60 are friction fit into the blocking notches 72 of a replacement instrument support 56. The replacement instrument support 56, and hence the nuts 60, are then slid into the channel 66 in the manner previously described above. The screws 62 are then re-engaged with the nuts 60 in the manner previously described above which thereby re-secures the instrument retainer assembly 50 to the bottom wall 22.

Figure 8:
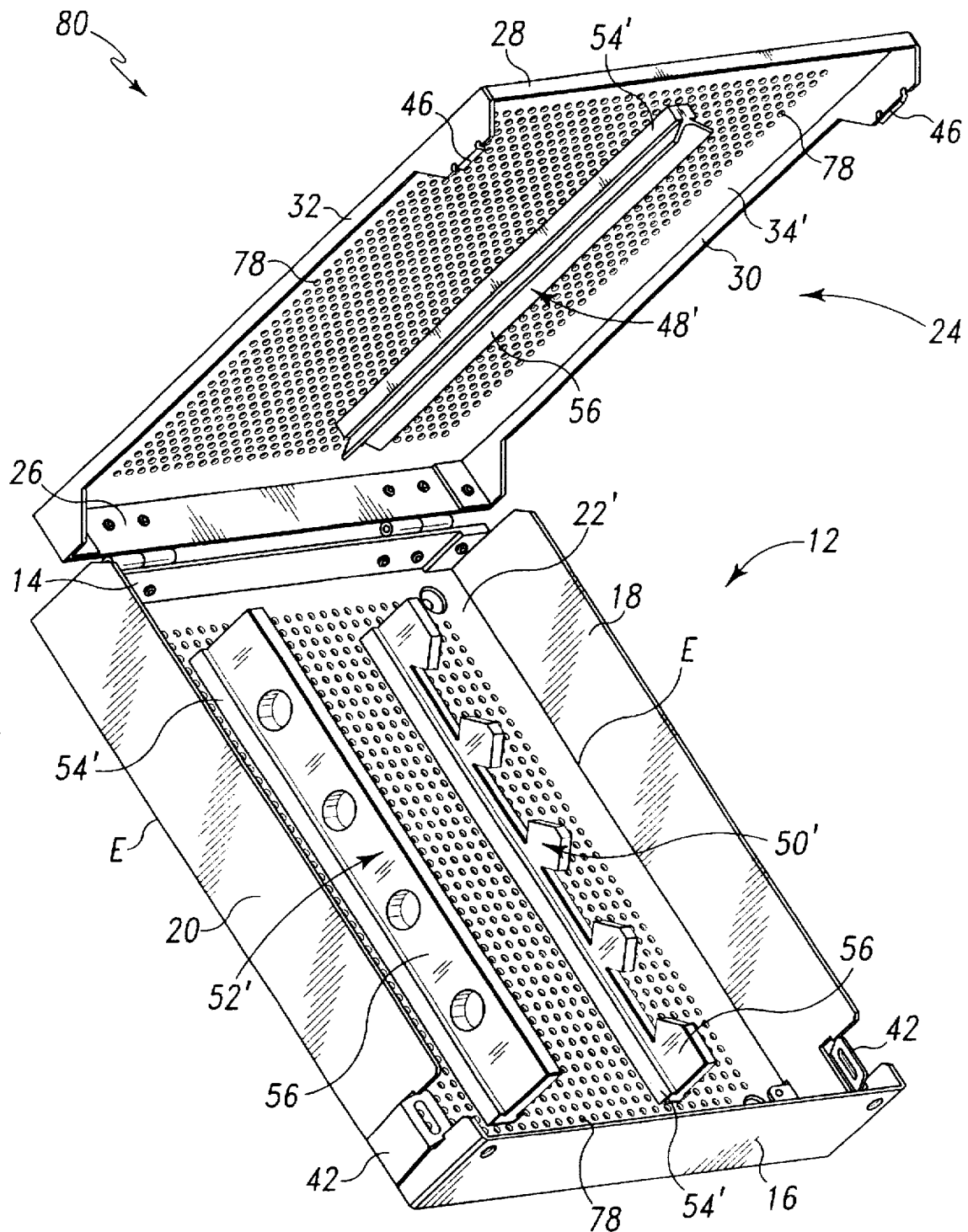
FIG. 8 is a perspective view of a second embodiment of an instrument cassette, which incorporates the features of the present invention therein, showing the instrument retainer assemblies positioned in a parallel orientation.
Figure 9:
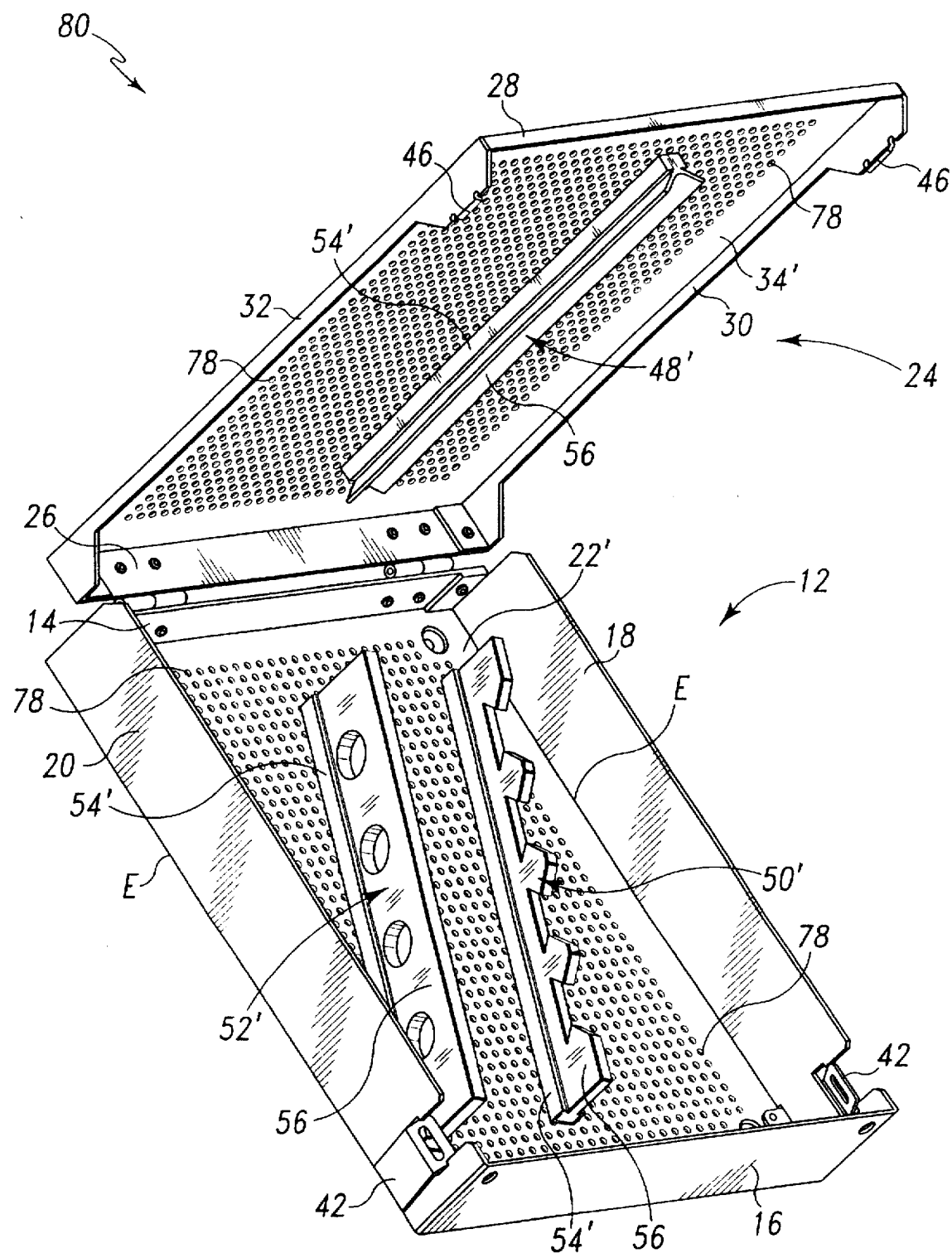
FIG. 9 is a view similar to FIG. 8, but showing the instrument retainer assemblies positioned in a diagonal orientation.

Referring now to FIGS. 8–9, there is shown an instrument cassette 80. The same reference numerals are used in FIGS. 8–9 to designate common components which were previously discussed in regard to FIGS. 1–7.

A bottom wall 22' and a top wall 34' of the instrument cassette 80 include a larger number of the positioning holes 78 relative the bottom wall 22 and the top wall 34 of the instrument cassette 10. Moreover, the fluid holes 36 included in the bottom wall 22 and top wall 34 of the instrument cassette 10 have been removed from the bottom wall 22' and the top wall 34' of the instrument cassette 80. Hence, the positioning holes 78 of the instrument cassette 80 function as both a hole for receiving the screws 62 of an instrument retainer assembly 48', 50', 52', and also as holes through which the sterilant is advanced.

It should be noted that the instrument retainer assemblies 48', 50', and 52' are substantially identical, except for the configuration of the various instrument supports 56' which are retained by a respective holder 54'. Therefore, only a detailed discussion of one of the instrument retainer assemblies (i.e. instrument retainer 50') will be necessary.

Figure 10:
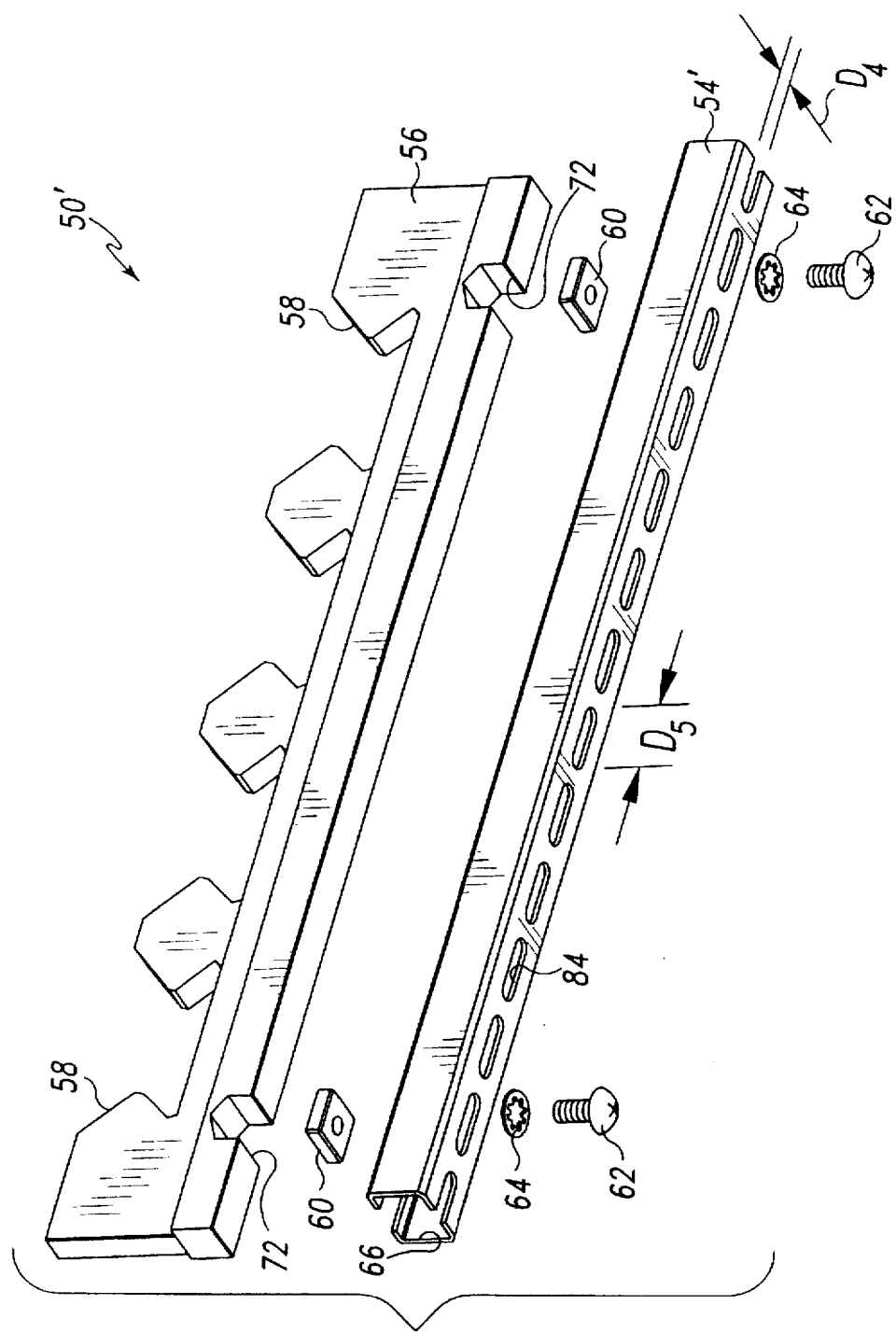
FIG. 10 is an enlarged exploded perspective view of one of the instrument retainer assemblies of the instrument cassette of FIG. 8.

The instrument retainer assembly 50' includes a holder 54'. The holder 54' is essentially the same as the holder 54 of the instrument retainer assembly 50, except that the plurality of holes 65 have been replaced by a plurality of elongated slots 84 as shown in FIG. 10. As shall be discussed in more detail below, the elongated slots 84 allow the instrument retainer assembly 50' to be secured within the instrument cassette in any one of numerous orientations in relation to a wall of the instrument cassette.

The dimensions of each of the elongated slots 84 enables the holder 54' to be secured within the instrument cassette at any one of numerous orientations. More specifically, at any given angle of placement of the holder 54' on the bottom wall 22' or the top wall 34', a number of the elongated slots 84 are positioned proximate a number of the positioning holes 78 so as to allow one of the screws 62 to be received through both the positioning hole 78 and the elongated slot 84. Each of the elongated slots 84 has a width of a distance $D_4$ as shown in FIG. 10, and a length of a distance $D_5$. Preferably, the distance $D_5$ is at least twice as large in magnitude as the distance $D_4$.

The instrument retainer assembly 50' is attached to the bottom wall 22' in a similar manner as the instrument retainer assembly 50 is attached to the bottom wall 22. More specifically, one of the lock washers 64 is inserted onto the screw 62 (see FIG. 10), and thereafter the screw 62 is received through one of the positioning holes 78 defined in the bottom wall 22' (see FIG. 8). The screw 62 is then received through one of the elongated slots 84 (see FIG. 10) defined in a first end of the holder 54'. After which, the screw 62 is threadingly engaged with a respective nut 60 disposed in the blocking notch 72. Another screw 62 is then engaged in a similar manner with a second nut 60 at the other end of the holder 54' thereby securing the instrument retainer assembly 50' to the bottom wall 22' as shown in FIG. 8.

The instrument retainer assembly 50' may be attached to the bottom wall 22' at an orientation which is parallel to the edges E of the bottom wall 22' as shown in FIG. 8. More specifically, the holder 54' may be positioned in a first or parallel orientation wherein the holder 54' is positioned in parallel relationship with the right edge E and the left edge E of the bottom wall 22'.

The instrument retainer assembly 50' may also be attached to the bottom wall 22' such that the instrument retainer assembly 50' is not parallel to the edges E of the bottom wall 22' as shown in FIG. 9. More specifically, the holder 54' may be positioned in a second or diagonal orientation wherein the holder 54' is positioned in a non-parallel relationship with each of the right edge E and the left edge E of the bottom wall 22' as shown in FIG. 9.

Referring now to FIGS. 11–14, the relationship between the holder 54', the bottom wall 22', and the screws 62 is shown. Note that the instrument support 56 has been removed for clarity of description. It should be appreciated that although the orientation of the holder 54' is discussed relative the bottom wall 22' in the following discussion, the holder 54' may also be orientated similarly relative the top wall 34'. Therefore, the following discussion relating to the orientation of the holder 54' relative the bottom wall 22' is also applicable to the orientation of the holder 54' relative the top wall 34'.

Figure 11:
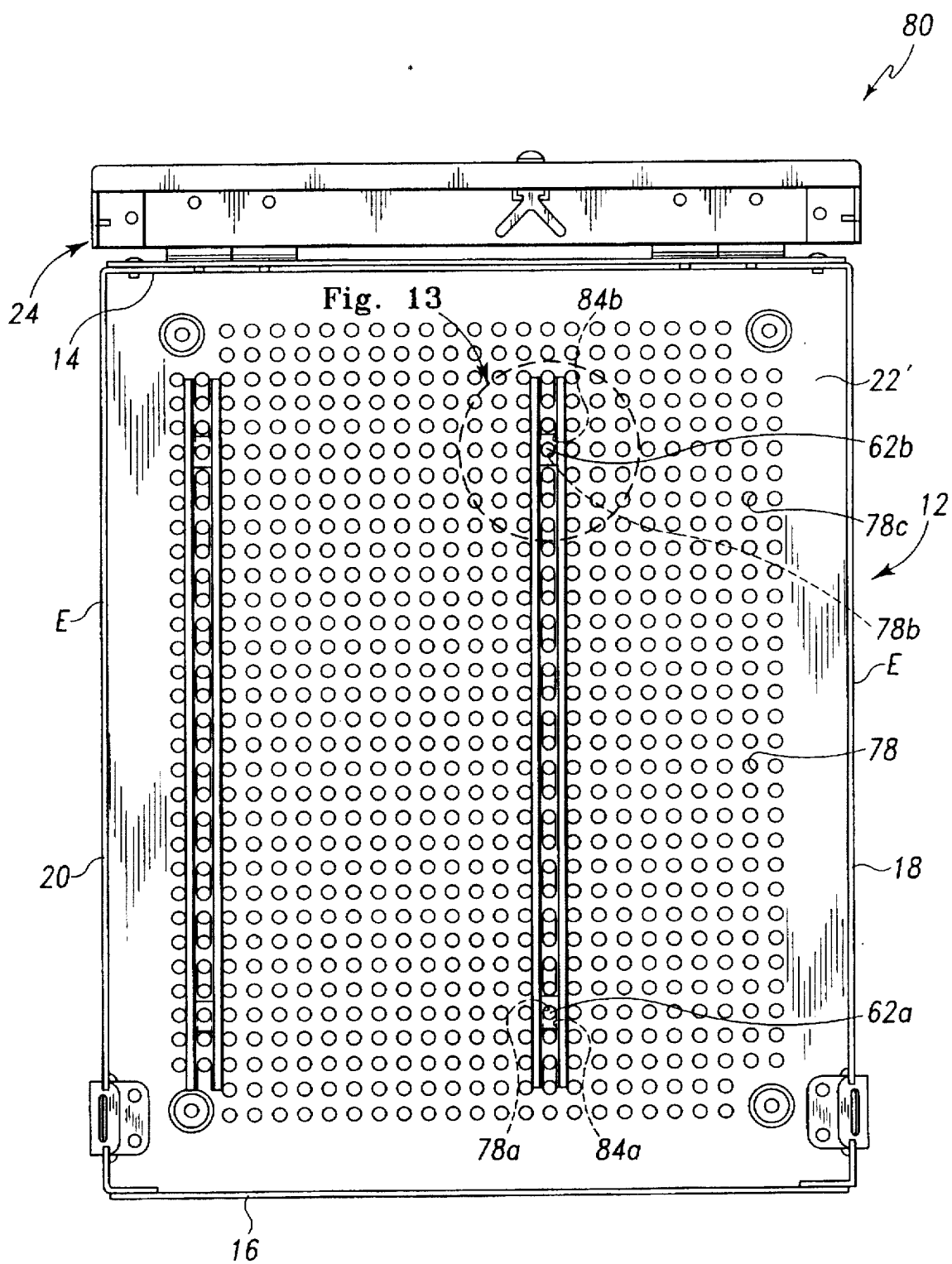
FIG. 11 is an enlarged top elevational view of the instrument cassette of FIG. 8 showing the holder positioned in the parallel orientation.

When the holder 54' is positioned in its parallel orientation as shown in FIG. 11, a screw 62a is received through a positioning hole 78a and into a first portion of an elongated slot 84a. Moreover, a screw 62b is received through the positioning hole 78b (see FIG. 12) and into a first portion of an elongated slot 84b.

Figure 12:
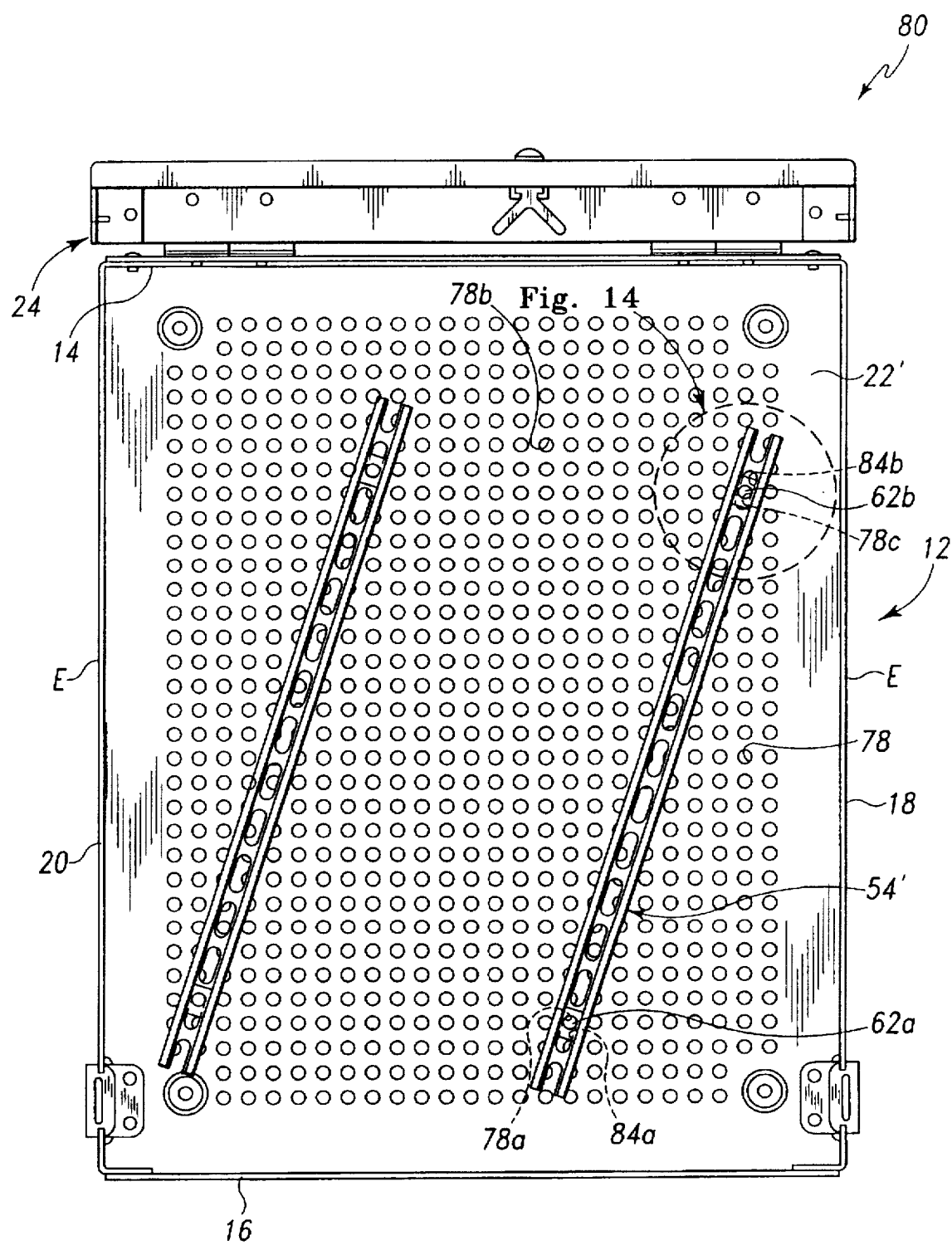
FIG. 12 is an enlarged top elevational view of the instrument cassette of FIG. 8 showing the holder positioned in the diagonal orientation.
Figure 13:
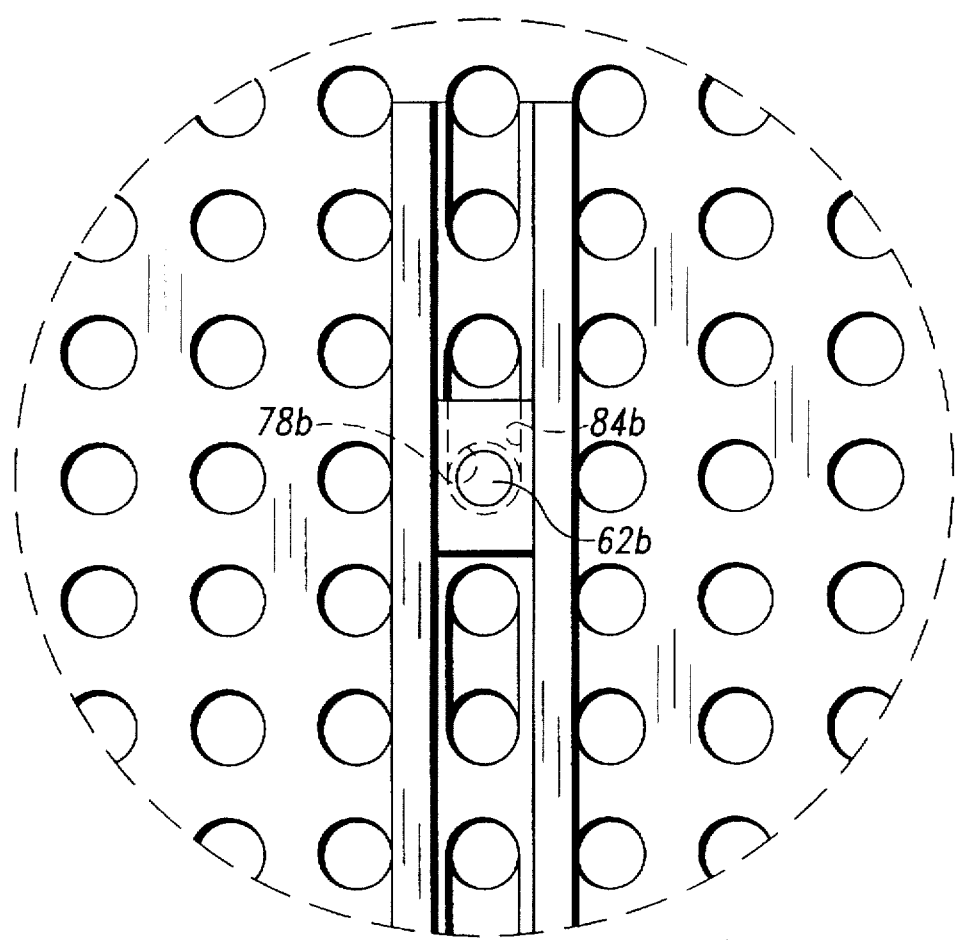
FIG. 13 is an enlarged view of a portion of FIG. 11 which is encircled and indicated as FIG. 13.
Figure 14:
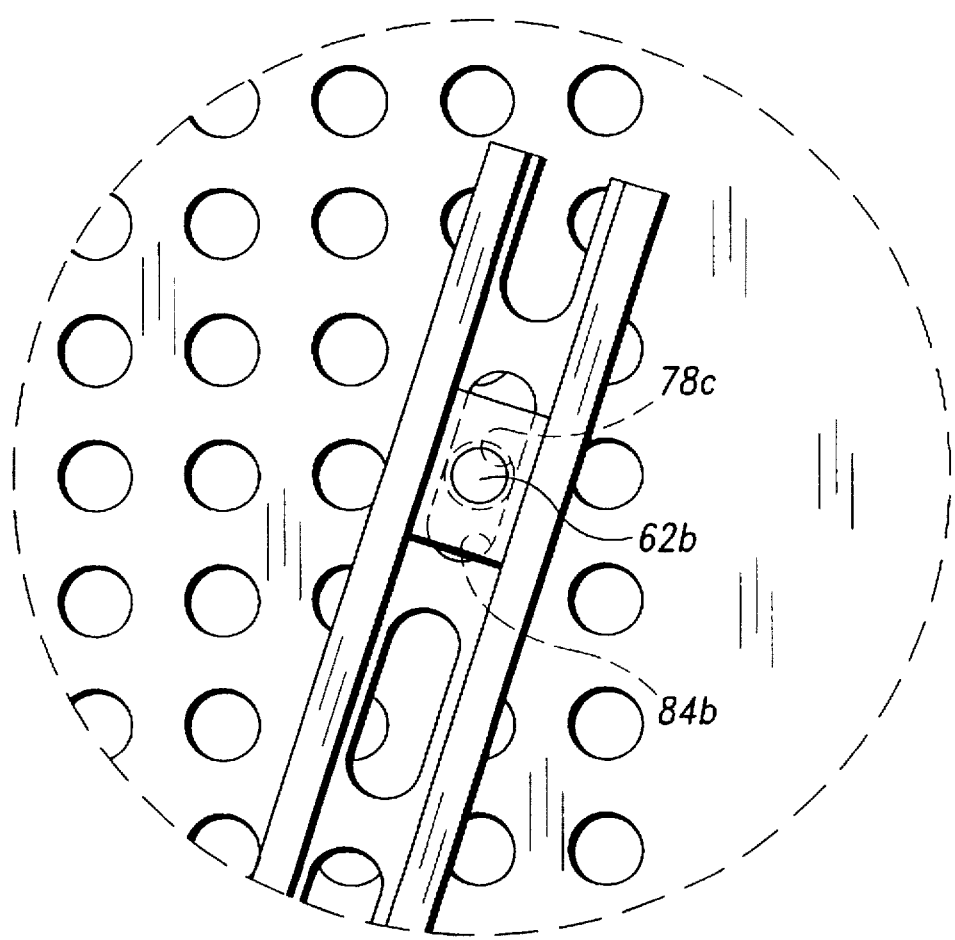
FIG. 14 is an enlarged view of a portion of FIG. 12 which is encircled and indicated as FIG. 14.

When the holder 54' is positioned in its diagonal orientation as shown in FIG. 12, the screw 62a is received through the positioning hole 78a and remains in the first portion of the elongated slot 84a. However, the screw 62b is removed from the positioning hole 78b and is received through a positioning hole 78c (see FIG. 11) and into a second portion of the elongated slot 84b.

It should be appreciated that although the holder 54' is shown secured through positioning hole 78a in both its parallel and diagonal orientations, the holder 54' may be secured through any of the positioning holes 78 included on the bottom wall 22' so long as each one of the screws 62a, 62b used to secure the instrument retainer assembly 50' to the bottom wall 22' are received into one of the elongated slots 84.

As described above, the nut 60 cooperates with the blocking notch 72 in order to prevent lateral movement of the instrument support 56, 56' relative the holder 54, 54'. In addition, the holder 54' allows for the instrument retainer assembly 50' to be placed in any one of numerous orientations relative to a wall of the instrument cassette, including a diagonal orientation, which provides numerous advantages over instrument cassettes which have heretofore been designed.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

What is claimed is:

1. An instrument cassette, comprising:

a wall having a first hole defined therein;

a holder having a channel and a second hole defined therein;

an instrument support positioned within said channel of said holder, said instrument support having a blocking notch defined therein;

a screw which extends through said first hole and said second hole; and a nut positioned within said blocking notch and secured to said screw, wherein said channel of said holder has a first width, and wherein said nut has a second width such that rotation of said nut is prevented when said nut is located within said channel.

2. An instrument cassette, comprising:

a wall having a first hole defined therein:

a holder having a channel and a second hole defined therein;

an instrument support positioned within said channel of said holder, said instrument support having a blocking notch defined therein;

a screw which extends through said first hole and said second hole; and a nut positioned within said blocking notch and secured to said screw, wherein said nut is friction fit within said blocking notch of said instrument support.

3. An instrument cassette, comprising:

a wall;

a holder secured to said wall;

an instrument support secured to said holder, said instrument support having a blocking notch defined therein; and a blocking member positioned within said blocking notch and secured to said holder, wherein said holder has a channel defined therein, wherein said channel has a first width, and wherein said blocking member has a second width such that rotation of said blocking member is prevented when said blocking member is located within said channel.

4. An instrument cassette, comprising:

a wall;

a holder secured to said wall;

an instrument support secured to said holder, said instrument support having a blocking notch defined therein; and a blocking member positioned within said blocking notch and secured to said holder, wherein said blocking member is friction fit within said blocking notch of said instrument support.

5. An instrument cassette, comprising:

a tray;

a lid pivotally attached to said tray;

a holder secured to said tray;

an instrument support secured to said holder, said instrument support having a blocking notch defined therein; and means, which cooperates with said blocking notch, for preventing lateral movement of said instrument support relative to said holder, wherein said preventing means includes (1) a nut, and (2) a screw which threadingly engages said nut, wherein said holder has a channel defined therein, wherein said channel has a first width, and wherein said nut has a second width such that rotation of said nut is prevented when said nut is located within said channel.

* * * * *